United States Patent [19]

Kajfež et al.

[11] 4,010,153

[45] Mar. 1, 1977

[54] PREPARATION OF CHIRAL 1,4-BENZODIAZEPIN-2-ONE-DERIVATIVES BY REACTION OF (S)-α-AMINO ACID CHLORIDE HYDROCHLORIDES ETC.

[75] Inventors: Franjo Kajfež; Vitomir Šunjić, both of Chiasso, Switzerland

[73] Assignee: CRC Compagnia di Ricerca Chimica S.A., Chiasso, Switzerland

[22] Filed: July 29, 1974

[21] Appl. No.: 492,912

[30] Foreign Application Priority Data

July 30, 1973 Switzerland .................... 11056/73

[52] U.S. Cl. .................... 260/239.3 D; 260/562 N; 424/244
[51] Int. Cl.² ...................... C07D 243/48
[58] Field of Search ............... 260/239.3 D

[56] References Cited

UNITED STATES PATENTS 3,371,085   2/1968   Reeder et al. .............. 260/239.3 D

FOREIGN PATENTS OR APPLICATIONS 44-26302   11/1967   Japan ......................... 260/239.3 D

OTHER PUBLICATIONS

Bell et al., "J. Org. Chem.," vol. 27, pp. 560–566 (1962).
Chemical Abstracts, vol. 80, (1974), p. 345, Item 70786m, Abstracting Sunjic et al., in "Acta Pharm. Jugoslav.," (1973), vol. 23, No. 4, pp. 213–217.
Sunjic et al., in "Acta Pharm. Jugoslav.," (1973), vol. 23, No. 4, pp. 213–217.
Sunjic et al., in "J. Het. Chem.," (1973), vol. 10, pp. 591–599.

*Primary Examiner*—Henry R. Jiles
*Assistant Examiner*—Robert T. Bond

[57] ABSTRACT

A process is disclosed for preparing optically active 1,4-diazepine-2-ones by reacting an acid chloride-hydrochloride of an optically active α-amino acid with a substituted o-amino benzophenone, to form an intermediate product and subsequently cyclizing the intermediate product to form the desired 1,4-diazepine-2-one. The process is carried out in inert organic or aqueous-organic solvents. The process eliminates the need for using α-amino acids having bound to the amino group a protective group which must be removed before cyclization.

9 Claims, No Drawings

PREPARATION OF CHIRAL 1,4-BENZODIAZEPIN-2-ONE-DERIVATIVES BY REACTION OF (S)-α-AMINO ACID CHLORIDE HYDROCHLORIDES ETC.

The invention relates to the preparation of optically active compounds of general formula I

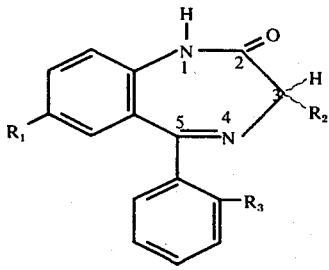

which have an asymmetric carbon atom in the 3-position wherein:

$R_1$ is a hydrogen atom, halogen atom, or alkoxy group, $R_2$ is a n- or iso-lower alkyl radial with at most four carbon atoms, a benzyl, p-hydroxybenzyl-, or 3'-methyleneindolyl group, and $R_3$ is a hydrogen atom or a halogen atom.

The compounds of general formula I can be made according to this process from compounds of general formula II

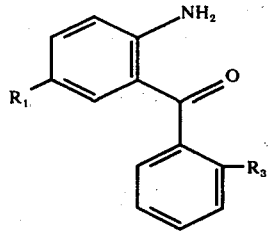

wherein $R_1$ and $R_3$ have the same significance as in formula I, by reacting with a compound of general formula III

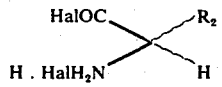

wherein $R_2$ has the same significance as in the compounds of general formula I, and Hal signifies a halogen atom.

In the course of the reaction intermediate compounds are formed having general formula IV

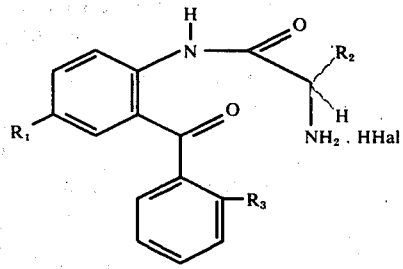

wherein $R_1$, $R_2$ and $R_3$ have the same significance as the formula above.

This new process for preparing the optically active 1,4-benzodiazepine-2-ones already described by us (U.S. application Ser. No. 234,645, filed Mar. 14, 1972, now abandoned) has been developed on the basis of the following information. Acid chloride-hydrochlorides of optically active alpha-amino acids are optically stable materials under the reaction conditions used for preparing compound IV. The hydrochloric acid in the reaction mixture is either bound to the amino group of the alpha-amino acid (since this has a pKa value between 9 and 10) or in the free state, since the 2-amino group in benzophenones has a vinylogous amide character and therefore exhibits very weakly basic properties.

The cyclization of the intermediate compound of formula IV takes place without isolating the free base in a homogeneous mixture of water and an organic solvent, or in a non-polar organic solvent. According to our earlier process (U.S. Patent application Ser. No. 234,645, now abandoned) the starting material is a protected alpha-amino acid while according to the new process acid chlorides of free alpha-amino acids in the form of salts with hydrochloric acid are used directly as participants in the reaction.

The obtained compounds can be used in the treatment of various psychic diseases, for example as muscle relaxants and tranquilizers. The (S)-forms of compounds of general formula I have been found to be especially active, and greatly surpass the corresponding (R)-forms in pharmacological activity. To further illustrate our invention the following examples are presented, which in no way limit the scope of this invention.

EXAMPLE 1

4.45 grams (50 millimoles) of L-alanine and 20.7 grams (100 millimoles) of phosphorus oxychloride were slurried in 100 milliliters of carbon tetrachloride previously dried with calcium chloride, and the mixture was stirred for 40 hours at room temperature with moisture being excluded. After the conclusion of the reaction a white thick suspension was obtained. This was filtered and the precipitate was washed three times with 30 milliliter portions of carbon tetrachloride and then without drying rapidly added to a solution of 12.1 grams of 2-amino-5-chlorobenzophenone in 200 milliliters of methylenechloride. The reaction was carried out for 20 hours at room temperature with agitation. Finally 100 milliliters of water were added to the reddish-brown solution and it was placed in a separatory funnel along with a 15% solution of sodium hydroxide having a pH of 9 to 9.5. The organic phase was separated and the aqueous layer was extracted twice with 50 milliliter portions of methylene chloride. The organic extracts were combined and dried with calcium chloride and amounted to about 100 milliliters. This solution was heated for two hours and at reflux temperature, then cooled and washed twice with 100 milliliter portions of hydrochloric acid (1 : 1) and twice with 100 milliliter portions of water. By this procedure the product 1,4-benzodiazepine-2-one was completely transferred to the aqueous phase, while the 2-amino-5-chloro-benzophenone remained behind in the organic phase. The organic phase was evaporated and, by recrystallization of the residue from 80% ethanol, 4.43 grams of the starting material were recovered. The acid aqueous phase was adjusted to a pH of 8 to 8.5 with cooling, and the precipitated crude product was filtered with suction and dried. 5.07 grams (46.1% of the theoretical, or 73% of the theoretical calculated on the consumed starting material) were obtained. The crude product was dissolved in 30 milliliters of warm acetone, the insoluble material filtered off, and finally 20 milliliters of warm water was added slowly. The mixture was cooled and there was recovered 3-(S)-methyl-7-chloro-5-phenyl-1,2-dihydro-2H-1,4-benzodiazepin-2-one in the form of long prisms melting at 200° C to 203° C (crystal transition between 170° C and 180° C), $[\alpha]_{578} + 207°$ ($c = 1.42$ CHCl$_3$).

EXAMPLE 2

1.65 grams (10 millimoles) of L-phenylalanine was converted by means of 5.2 grams (25 millimoles) of phosphorus pentachloride in 80 milliliters of carbon tetrachloride into the acid chloride-hydrochloride by a procedure analogous to that described in Example 1. The crude acid chloride hydrochloride was filtered with suction, washed three times with 20 milliliter portions of methylene chloride, and added to a solution of 1.85 grams (2.0 millimoles) of 2-amino-5-chlorobenzophenone in 120 milliliters of methylene chloride. The reaction mixture was stirred for 24 hours at room temperature with moisture being excluded. 80 milliliters of water was then added and the two phase system was adjusted to pH 9 with vigorous agitation. The organic layer was separated and the aqueous phase was extracted twice with 50 milliliter portions of methylene chloride. The organic extracts were combined, dried (CaCl$_2$), concentrated to 50 milliliters, and then heated for two hours at reflux temperature. After cooling the mixture was washed three times with 50 milliliter portions of hydrochloric acid (1 : 1) and three times with 50 milliliter portions of water. All the aqueous extracts were combined, adjusted to pH 8 with alkali, and extracted three times with 100 milliliter portions of ether. The ether phase contained 3-(S)-benzyl-7-chloro-5-phenyl-1,2-dihydro-2H-1,4-benzodiazepin-2-one which after drying, evaporation, and recrystallization from cyclohexane yielded 1.04 grams, melting point 107° C to 110° C, $[\alpha]_{578} + 50.4°$ ($c = 0.65$, CHCl$_3$).

EXAMPLE 3

From 17.5 grams (0.15 millimoles) of L-Valine the corresponding chloride-hydrochloride was prepared by treatment with 62 grams of phosphorus pentachloride in 500 milliliters of methylene chloride for 48 hours. The product was filtered, washed with methylene chloride, and directly condensed with 28.7 grams (120 millimoles) of 2-amino-5-chloro-benzophenone in 1 liter of methylene chloride. After stirring for 24 hours at room temperature the residual alpha-amino acid was removed by extracting with dilute base at pH 9. The organic phase was dried and heated to reflux temperature for 2 hours, and the unreacted 2-amino-5-chlorobenzophenone was separated by extraction with three portions of 200 milliliters each of hydrochloric acid (1 : 1). The aqueous phase was adjusted to a pH of 8 and extracted three times with 100 milliliter portions of ether. The ether extract dried (Na$_2$SO$_4$) and evaporated to dryness, and the crude 3-(S)-isopropyl-7-chloro-5-phenyl-1,2-dihydro-2H-1,4-benzodiazepin-2-one was recrystallized from petroleum ether (40° to 60° C). 20.5 grams was obtained, melting point 190° C to 193° C, $[\alpha]_{578} + 145°$ ($c = 0.885$, CHCl$_3$).

EXAMPLE 4

Starting from 18.1 grams (100 millimoles) of L-tyrosine the acid chloride-hydrochloride was prepared in 500 milliliters of methylene chloride by treatment with 41.5 grams (200 millimoles) of phosphorus pentachloride. The acid chloride-hydrochloride was further reacted with 19.1 grams (90 millimoles) of 2-amino-5-chlorobenzophenone in 400 milliliters of methylene chloride for 30 hours. The crude product was isolated in a manner similar to that described in Examples 2 and 3. 14.2 grams of 3-(S)-p'-hydroxybenzyl-7-chloro-5-phenyl-1,2-dihydro-2H-1,4-benzodiazepin-2-one were obtained, melting point 142° C to 144° C, $[\alpha]_{578} + 41°$ ($c = 0.774$, CHCl$_3$).

EXAMPLE 5

From 10.2 grams (50 millimoles) of L-tryptophane the acid chloride-hydrochloride was prepared by reaction with 20.8 grams (100 millimoles) of phosphorus pentachloride in 300 milliliters of dry, freshly distilled chloroform. The filtered product was added to a solution of 13.8 grams (60 millimoles) of 2-amino-5-chloro-benzophenone in 200 milliliters of tetrahydrofuran. The reaction was carried out for 48 hours at room temperature with stirring. The product was isolated as described in Examples 2 and 3. There was obtained 3-(S)-(3'-indolyl)-methyl-7-chloro-5-phenyl-1,2-dihydro-2H-1,4-benzodiazepin-2-one, melting point 148° C to 150° C (from ether), $[\alpha]_{578} + 41.8°$ ($c = 1.00$, CHCl$_3$).

EXAMPLE 6

From L-alanine (2.23 grams, 25 millimoles) and 10.35 grams (50 millimoles) of phosphorus pentachloride L-alanyl chloride-hydrochloride was prepared in 60 milliliters of carbon tetrachloride by the procedure described in Example 1. The product was added to a solution of 7.02 grams (25 millimoles) of 2-amino-2',5-dichlorobenzophenone in 120 milliliters of methylene chloride. The reaction was carried out for 48 hours at room temperature with exclusion of moisture and with stirring. Finally 80 milliliters of water were added and the mixture was placed in a separatory funnel with a 15% solution of NaOH at pH 9. The organic phase was separated and the aqueous layer was extracted twice with 50 milliliter portions of methylene chloride. The organic extracts were combined, dried, concentrated to 80 to 100 milliliters, and then heated for three hours to reflux temperature. The solution was cooled and washed twice with 50 milliliter portions of hydrochloric acid (1 : 1) and then twice with 100 milliliter portions of water. The acid aqueous phase was adjusted with cooling to pH 8, and the precipitated crude product was filtered and dried. There was obtained about 2.5 grams, melting point 165° C to 170° C. After recrystallization from acetone-water the melting point was 172° C to 173° C, $[\alpha]_{578} + 65.7°$ ($c = 1.730$ in methanol).

We claim:

1. A process preparing optically active 1,4-benzodiazepin-2-ones with (S)-configuration in the 3-position having the formula I

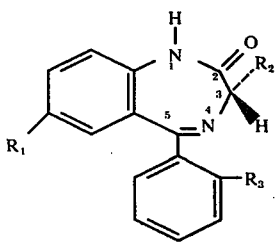

wherein $R_1$ is a hydrogen atom, or a halogen atom, $R_2$ is an n- or iso- lower alkyl radical with at most 4 carbon atoms, a benzyl, p-hydroxybenzyl, or 3′-methyleneindolyl group, $R_3$ is a hydrogen atom or a halogen atom, comprising the steps of (a) reacting, in an inert solvent selected from methylene chloride and tetrahydrofuran at about room temperature, a compound of the formula II

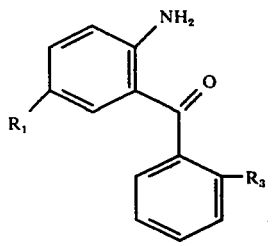

wherein $R_1$ and $R_3$ have the same significance as in Formula I with a compound of the formula III in the (S)-configuration

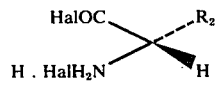

in which $R_2$ has the same significance as in Formula I and Hal is a halogen atom, whereby an intermediate compound of the formula IV in the (S)-configuration is formed, and

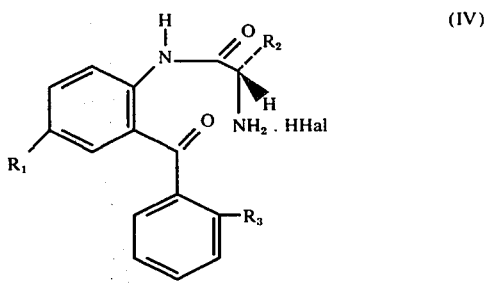

(b) cyclizing said intermediate compound in an inert solvent selected from the group consisting of a homogeneous mixture of water and an organic solvent and non-polar organic solvents, at a temperature of up to about 40° C whereby the compound of Formula I in the (S)-configuration is formed.

2. A process according to claim 1 wherein step (a) is carried out at room temperature for a period between 20 and 48 hours.

3. A process according to claim 1 wherein step (b) is carried out in methylene chloride at the reflux temperature of the solvent for a period of 2 to 3 hours.

4. A process according to claim 1 wherein said compound of formula II is L-phenylalanine.

5. A process according to claim 1 wherein said compound of formula II is L-valine.

6. A process according to claim 1 wherein said compound of formula II is L-tyrosine.

7. A process according to claim 1 wherein said compound of formula II is L-tryptophane.

8. A process according to claim 1 wherein said compound of formula III is 2-amino-5-chlorobenzophenone.

9. A process according to claim 1 wherein said compound of formula III is 2-amino-2′,5-dichlorobenzophenone.

* * * * *